(12) United States Patent
Hoffpauer

(10) Patent No.: US 7,700,142 B2
(45) Date of Patent: Apr. 20, 2010

(54) FORTIFIED CEREAL BRAN TO PROMOTE DIGESTIVE HEALTH

(76) Inventor: Diane Wright Hoffpauer, P.O. Box 393, Crowley, LA (US) 70526

( * ) Notice: Subject to any disclaimer, the term of this patent is extended or adjusted under 35 U.S.C. 154(b) by 1292 days.

(21) Appl. No.: 11/130,008

(22) Filed: May 16, 2005

(65) Prior Publication Data

US 2006/0257530 A1  Nov. 16, 2006

(51) Int. Cl.
*A23L 1/302* (2006.01)
*A23L 1/10* (2006.01)

(52) U.S. Cl. .......................... 426/74; 426/72; 424/439; 424/750; 424/808; 514/558; 514/559

(58) Field of Classification Search ................ 424/750; 426/619, 621
See application file for complete search history.

(56) References Cited

U.S. PATENT DOCUMENTS

| | | | |
|---|---|---|---|
| 1,431,938 A | 10/1922 | Dunham | |
| 1,432,057 A | 10/1922 | Dunham | |
| 3,418,656 A | 12/1968 | Vassiliades | |
| 3,993,831 A | 11/1976 | Vassiliades | |
| 5,009,900 A | 4/1991 | Levine et al. | |
| 5,087,461 A | 2/1992 | Levine et al. | |
| 5,106,639 A | 4/1992 | Lee et al. | |
| 5,211,980 A | 5/1993 | Cox | |
| 5,976,603 A | 11/1999 | Kota et al. | |
| 6,017,550 A | 1/2000 | Berk et al. | |
| 6,251,478 B1 | 6/2001 | Pacifico et al. | |
| 6,436,431 B1 | 8/2002 | Hoffpauer et al. | |
| 6,569,445 B2 * | 5/2003 | Manning et al. | 424/439 |
| 6,733,799 B2 | 5/2004 | Cheruvanky et al. | |
| 6,737,089 B2 | 5/2004 | Wadsworth et al. | |
| 2002/0102330 A1 | 8/2002 | Schramm et al. | |
| 2003/0031768 A1 | 2/2003 | Dalziel et al. | |
| 2004/0162268 A1 | 8/2004 | Cimiluca et al. | |

OTHER PUBLICATIONS

Jacobs, et al; "Whole-Grain Intake and Cancer: An Expanded Review and Meta-Analysis", Nutrition and Cancer, 30(2), pp. 85-96.
"Omega Grand"; http://www.enreco.com/enreco/Products/omegagrande.htm; Mar. 29, 2005.
Golden Sunrise Nutri-Rice; "The Story of an All Natural Rice Bran Revealed"; http://www.nutri-rice.com/story.html; Mar. 29, 2005.
CopRice Specialty Products; "CopRice Chook Pellets"; http://www.coprice.com.au/specialty/poultry/chookpellets.asp; Mar. 29, 2005.
Golden Sunrise Nutri-Rice; "Vitamins"; http://www.nutri-rice.com/vitamins.html; Mar. 30, 2005.
Golden Sunrise Nutri-Rice; "Minerals"; http://www.nutri-rice.com/minerals.html; Mar. 30, 2005.
Golden Sunrise Nutri-Rice; "Antioxidants"; http://www.nutri-rice.com/antioxidants.html; Mar. 30, 2005.
Scientific Research on Noni Fruit; "Recent Scentific Studies on Morinda Citrifolia (Noni)"; http://www.occi.com/-fisher/noni/studies.htm; Mar. 30, 2005.
Ecology Health Center; "Diverticulitis Intestinal Inflammation from Crohns.net"; http://www.crohns.net/Miva/education/diverticulitis.shtml; Apr. 28, 2005.
NutraCea Inc. Product, Cea100® Supplemental Facts, Apr. 2004, entire document.
National Academy of Sciences Book, 10th ed., 1989 Dietary Reference Intakes: National Academy of Sciences, 1997, Calcium, Phosphorous, Magnesium, Vitamin D and Fluoride, Abstract only.
Taylor, "Bran tablets and diverticular disease", *British Medical Journal*, Apr. 24, 1976, vol. 1, pp. 988-990.
Covington, "Omega-3 Fatty Acids", *American Family Physician*, vol. 70, No. 1, Jul. 1, 2004, pp. 133-140.
Jacobs, Jr. et al, "Whole-Grain Intake and Cancer: An Expanded Review and Meta-Analysis", *Nutrition and Cancer*, 30(2), 1998, 85-96.
Hill, MJ, Cereals, "cereal fibre and colorectal cancer risk: a review of the epidemiological literature", *Eur. J. Cancer Prevention*, 6, 1997, pp. 219-225.
Fabio, L. et al., "Dietary Factors and the Risk of Endometrial Cancer", *Cancer* 57, 1993, pp. 3575-3581.
Goodman, M.T. et al., "Association of Soy and Fiber Consumption with the Risk of Endometrial Cancer", *Am. J. Epidemiol.*, 146, 1997, 294-306.
Slattery, M.L. et al., "Plant foods and colon cancer: an assessment of specific foods and their related nutrients" (United States), *Cancer Causes and Control*, vol. 8, 1997, 575-590.

(Continued)

*Primary Examiner*—Jennifer McNeil
*Assistant Examiner*—Hong Mehta
(74) *Attorney, Agent, or Firm*—Buchanan Ingersoll & Rooney PC

(57) ABSTRACT

A cereal bran fortified with an effective amount of select additives such as vitamins, minerals, and essential dietary fats to promote digestive health. The fortified cereal bran can be used as a dietary supplement or as an added ingredient to fortify various food products. The additive used herein is an effective amount of vitamin D, selenium, calcium, magnesium, folic acid and omega 3 fatty acids.

25 Claims, No Drawings

OTHER PUBLICATIONS

Witte, J.S. et al., "Relation of Vegetable, Fruit, and Grain Consumption to Colorectal Adenomatous Polyps", *Am. J. Epidemiol.* 144, 1996, 1015-1025.

Champagne, E.T., editor, *Rice: Chemistry and Technology, 3rd Ed.*, American Association of Cereal Chemists, Inc., St. Paul, MN, 2004, pp. 88-183.

U.S. FDA, Center for Food Safety and Applied Nutrition, Office of Nutritional Products, Labeling and Dietary Supplements: *Letter Regarding Dietary Supplement Health Claim for Fiber with Respect to Colorectal Cancer*, Oct. 10, 2000.

Lipkin, M. et al., The Protective Effects of Calcium and Vitamin D against Colon Cancer, *IFT Annual Meeting Book of Abstracts*, 1992, p. 67.

Lipkin, M., "Preclinical and Early Human Studies of Calcium and Colon Cancer Prevention", *Annals of the New York Academy of Sciences*, 889, 1999, 120-127.

Brett, A.S., "Calcium and Vitamin D: Partners in Preventing Colorectal Adenomas?", *Journal Watch*, Jan. 20, 2004.

Jacobs, E.T. et al., "Research and Public Health Implications of the Intricate Relationship between Calcium and Vitamin D in the Prevention of Colorectal Neoplasia", *J. of the Nat'l. Cancer Inst.*, vol. 95, No. 23, Dec. 3, 2003, 1736-1737.

Kim, Young-In, "Role of Folate in Colon Cancer Development and Progression", *The American Society for Nutritional Sciences*, J. Nutr., Nov. 2003, 133:3731S-3739S.

http://nutraingredients.com/news/news-NG.asp?n=37893-selenium, Selenium may prevent oesophageal cancer, NOVIS, May 21, 2003.

http://nutraingredients.com/news/news-ng.asp?id=56134&n=dt323&c=aldts, Higher selenium intake may reduce colorectal cancer risk, NOVIS, Nov. 18, 2004.

Sipos, P. et al., "Damaging effect of oxidized bile on colonic mucosa and the protective mechanism of an antioxidase", *Magy Seb.*, 56 (3-4): Aug. 2003, 123-6.

Ju, J. et al., "Effects of green tea and high-fat diet on arachidonic acid metabolism and aberrant crypt foci formation in an azoxymethane-induced colon carcinogenesis mouse model", *Nutr. Cancer*, 2003, 46(2), 172-8.

Cashman, K. et al., "Crohn's Disease Patients have Low Vitamin K Status", *Am. J. Gastroenterology* 2004, 99:2178-2185.

Belluzi, A., et al., "Effect of an Enteric-coated Fish-Oil Preparation on Relapses in Crohn's Disease", *The New England Journal of Medicine*, Vo. 334, No. 24, Jun. 13, 1996, 1557-1560.

Rose, DP, et al., "Omega 3 fatty acids as cancer chemopreventative agents", *Pharmacol. Ther.*, Sep. 1999, 83(3):217-44.

Jordan, A. et al., "Effect of an omega 3 fatty acid containing lipid emulsion alone and in combination with 5-fluorouracil (5-FU) on growth of the colon cancer cell line Caco-2", *Eur. J. Nutr.*, Dec. 2003, 42(6): 324-31.

Kuntz, L. et al., "Building a better breakfast cereal", Jan. 4, 1998, pp. 1-8, URL:http://www.foodproductdesign.com/articles/463/463_0498CS.HTML, retrieved on Jul. 8, 2008.

Saunders, R.M., "The Properties of Rice Bran as a Foodstuff," Cereal Foods World, 1990, 35:632.

Marshall, W.E. et al. (editors), Rice Science and Technology, 1994, Marcel Dekker, Inc., New York, pp. 384-389.

Ichimura, Y., et al., Effects of Gamma-Oryzanol on Gastric Lesions and Small Intestinal Propulsive Activity in Mice, 1984, *Nippon Yakurigaku Zasshi* 84(6): 537-542.

Itaya, K., et al., Studies of Gamma-Oryzanol (1). Effects on Stress-Induced Ulcer, 1976, *Nippon Yakurigaku Zasshi* 72(4): 475-481.

Hornstra, G., Omega-3 long chain polyunsaturated fatty acids and health benefits, *Roche Vitamins Europe Ltd*, 2002.

P.A. Lachance, "Food Service Nutrition: A Perspective From Academe", Dept. of Food Science, Rutgers University, New Brunswick, NJ, *1992 IFT Annual Meeting*, New Orleans, Louisiana, *Book of Abstracts*, Institute of Food Technologist, Chicago, Illinois, p. 193.

* cited by examiner

FORTIFIED CEREAL BRAN TO PROMOTE DIGESTIVE HEALTH

FIELD OF THE INVENTION

The present invention relates to a cereal bran fortified with an effective amount of select additives such as vitamins, minerals, and essential dietary fats to promote digestive health. The fortified cereal bran can be used as a dietary supplement or as an added ingredient to fortify various food products. The additive used herein is an effective amount of vitamin D, selenium, calcium, magnesium, folic acid and omega 3 fatty acids.

BACKGROUND OF THE INVENTION

The digestive tract is a major component of the gastrointestinal system. Essentially, it is a tube about five meters in length of variable cross-sectional areas running from mouth to anus that includes the mouth, pharynx, esophagus, stomach, small intestine, large intestine, which includes the colon, also known as the bowel. In the digestive tract, food is propelled by muscular contractions through its different regions. These contractions are referred to as peristalsis. Eventually, unabsorbed food residues are moved to the end of the tract and are eliminated from the body in the form of solids, semi-solids or liquids.

As used herein the term "digestive tract" includes, but is not limited to, the mouth, pharynx, esophagus, stomach, small intestine, large intestine, and pancreas. The digestive track can suffer from various disorders including diverticulitis, ulcerative colitis, Crohn's disease, diabetes, heartburn, Gurd's disease as well as cancers of the esophagus, pancreas, stomach, small and large intestine and colorectal.

It is believed that the main cause of some of the diseases, such as diverticulitis, of the digestive tract is due to a low-fiber diet, which is a direct result of the processed foods that are a major part of the American diet. Many processed foods contain refined, low-fiber flour. Unlike whole-wheat flour, refined flour has no wheat bran. Diverticulitis and diverticulosis disease is common in developed or industrialized countries where low-fiber diets are common and rare in countries of Asia and Africa, where high-fiber diets are common. It has also been suggested that diets low in saturated fatty acids and cholesterol and high in whole grain cereals have a protective effect against certain cancers. Thus, modifying one's diet can have beneficial effects on the digestive tract, especially by incorporating into the diet specific additives. Based on a 2000 calorie diet, the US Food and Drug Administration defines a product as "a good source of fiber" if it provides 10 percent of the Daily Value (DV)—2.5 grams of fiber per serving. A product is "high in", "rich in" or an "excellent source of fiber" if it provides 20 percent of the DV—5 grams of fiber per serving. Further, the US Department of Agriculture recommends 25 to 30 grams of fiber per day from fruits, vegetables or fiber-containing grain products. Specifically the USDA guidelines recommend 6 to 11 servings per day of cereal and grain foods. Typically cereal brans, including rice, wheat, barley, rye, oat, sorghum and millet have crude fiber ranging from approximately 7 to 20 percent at 14% moisture.

While various high-fiber products are commercially available for promoting digestive health, there is still a need in the art for products that are even more beneficial for the digestive tract.

SUMMARY OF THE INVENTION

The present invention provides a functional food product that is designed to prevent digestive tract disease by providing nutrients that prevent and treat at least one disorder of the digestive tract. The food product contains vitamins such as vitamin D and folic acid; minerals such as selenium, calcium, and magnesium; and omega 3 fatty acids, preferably from fish oil; with a cereal bran as the carrier or base for the product. The properties of the bran also contribute to digestive health-providing benefits of the product because of the bran's inherent fiber and other nutrients. The food product contains the nutrients in quantities that promote a healthy digestive system and that will prevent, and, in some cases, reverse the effects of at least one disorder of the digestive tract.

In accordance with the present invention there is provided a cereal bran product that is beneficial for promoting digestive health, which product is comprised of:
  a) cereal bran as a carrier;
  b) about 10 to 800 International Units of vitamin D per 30 grams of bran;
  c) about 20 to 200 mcg of selenium per 30 grams of bran;
  d) about 50 to 2000 mg of calcium per 30 grams of bran;
  e) about 10 to 500 mg of magnesium per 30 grams of bran;
  f) about 0.1 to 2 mg of folic acid per 30 grams of bran; and
  g) about 150 to 3000 mg of omega 3 fatty acids per 30 grams of bran; wherein said cereal bran can be comprised of one of a single cereal or a mixture of cereals.

The fortified bran of this invention is preferably in the form of a stabilized powder that is easily used as a dietary supplement or that can be added as an ingredient to a variety of foods to fortify the levels of the named nutrients in the food. Thus, a further aspect of this invention is directed to a food article containing the fortified cereal bran food product.

The present invention also provides a method of preventing and/or treating disorders of the digestive tract in an animal, involving the step of orally administering a therapeutically effective amount of the food product of this invention to the animal for a therapeutically effective period of time.

In a preferred embodiment the bran is a rice bran and one or more food-grade preservatives and/or antioxidants are added.

In yet another preferred embodiment one or more emulsifiers, surfactants and/or flow aid is present to enhance mixing properties.

DETAILED DESCRIPTION OF THE INVENTION

The present invention is a fortified cereal bran product that is capable of promoting digestive health. As previously mentioned the digestive track is susceptible to various disorders, some of which are caused by a low-fiber diet. Insoluble fiber may diminish the risk of some cancers by decreasing transit time in the gastrointestinal tract and aiding in the excretion of potentially carcinogenic waste products and reducing the hyperproliferation of cells. Soluble fiber reduces the glucose response and may prevent disorders such as diabetes. Low concentrations of various vitamins, minerals and essential fatty acids can also aggravate such disorders. The fortified cereal bran product of the present invention is a single source product providing all the necessary ingredients to aid in digestive health.

Non-limiting example of cereal brans suitable for use herein include the brans of wheat, rice, barley, sorghum, millet, rye, oats, and soy. It is believed that the bran alone, particularly rice bran, has components that act synergistically to prevent lesions associated with digestive diseases and disorders. The content of the various brans suitable for use in this invention is similar. For example, rice bran (and polish) contains significantly higher ranges of fat (15 to 19.7%) as compared to the other grains and higher thiamine (12 to 24%). It is to be understood that the cereal bran used in the practice of the present invention can have a fat content from fully fatted to substantially fully defatted. It is preferred to use fully fatted cereal bran. That is, cereal bran that contains its natural content of fat. It will also be understood that the cereal bran used as the carrier in this invention can be of a single cereal of a mixture of cereals. That is, each bran particle can be of a single cereal or a composite of two or more cereals. The cereal bran can also be a mixture of two or more cereal brans with each bran particle being of a single cereal. Rice bran, particularly fatted stabilized rice bran, is the most preferred cereal bran for use in the present invention.

Unfortunately, rice bran becomes rancid soon after milling. Lipase enzyme attacks the oil once the bran structure has been destroyed, and free fatty acid levels build up very quickly. The bran quickly develops a bad taste and odor. Several commercial techniques are used to stabilize rice bran, such as a method wherein a simple dry heat extruder is used to reach a temperature of about 270° F. for a short period of time. This temperature deactivates the lipase enzyme. The temperature range is critical. Too low and the lipase is not deactivated, too high and vitamin E (tocopherol) components are destroyed. The vitamin E components prevent oxidative rancidity over a long period of time. The process is relatively simple and when done properly, the bran is safe from both enzymatic and oxidative rancidity.

Several components of cereal bran, particularly rice bran, are desirable for the human diet. Rice bran protein has a high nutritional value that is highly digestible and is hypoallergenic. The proximate composition of stabilized, parboiled, defatted rice bran as stated in Saunders, R. M., "The Properties of Rice Bran as a Foodstuff", Cereal Foods World, 35:632 (1990), is as follows: moisture—6 to 9%, protein—23 to 27%; fat—0.5 to 1.5%, crude fiber—16 to 20%, and ash—11 to 14%. The fatty acid composition of the rice bran oil consists mainly of oleic, palmitic, and linoleic acids. In addition to the fatty acids, naturally occurring vitamins and minerals are present in varying amounts depending on growing conditions and milling methods. Vitamins and minerals present include vitamin A, thiamine, riboflavin, niacin, pyridoxine, panothenic acid, biotin, myoinositol, choline, para-aminobenzoic acid, folic acid, vitamin B.sub.12, vitamin E, calcium, iron, magnesium, manganese, phosphorus, potassium and zinc. The major carbohydrates present are cellulose, hemicelluloses (pentosans), and starch. Beta-glucans are also present, forming part of the dietary fiber complex. Total dietary fiber content ranges from about 44% to about 51%, with the soluble fiber constituting from 2.4% to 2.9% of that total (see Marshall, W. E. and Wadsworth, J. J (editors), Rice Science and Technology, Marcel Dekker, Inc., New York, pp. 384-389 (1994)).

Several nutrients important to digestive health however, are either low or absent in cereal bran. Such nutrients include the additives used herein to fortify the bran. These nutrients are vitamin D, selenium, calcium, magnesium, folic acid, and omega 3 acids. The bran of the present invention is used as a carrier for these nutrients and the preferred concentration range of each nutrient is: about 10 to 800 International Units (IU), more preferably about 25 IU to 400 IU of vitamin D; about 20 mcg to 200 mcg selenium; about 50 mg to 2000 mg, more preferably about 300 mg to 1800 mg of calcium; about 10 mg to 500 mg, more preferably about 40 mg to 350 mg of magnesium; about 0.1 mg to 2 mg, more preferably about 0.2 mg to 2 mg, most preferably about 0.4 mg to 2 mg of folic acid; and about 150 mg to 3000 mg, more preferably about 200 mg to 2000 mg, most preferably 300 mg to 1000 mg of omega 3 fatty acids. The omega 3 fatty acids can be those derived from fish oil that contain eicosapentaenoic acid (EPA) and docosahexaenoic acid (DHA) or those derived from dark green leafy vegetables, flaxseed oils etc and include alpha-linolenic acid (ALA). Omega 3 fatty acids derived from fish oils are preferred. Although ALA has different effects on the body than EPA and DHA, the body has enzymes that can convert ALA to EPA. All three fatty acids are important to human health. Zinc can also be used in addition to the above nutrients in the amount of about 20 to 3000 mg, preferably from about 1800 to 3000 mg. All amounts are based on 30 grams of bran or an effective amount of bran to produce at least a "good source of dietary fiber".

In addition to the above ingredients, the food product of this invention may contain one or more of other nutrients. Non-limiting examples of such other nutrients include vitamin A, riboflavin, pantothenic acid, niacin, biotin, myoinositol, choline, para-aminobenzoic acid, α tochopherol (E), copper, iron, manganese, phosphorus, potassium, zinc, carbohydrates (such as cellulose, hemicellulose and starch), beta-glucans, and one or more fatty acids, other than omega 3 fatty acids from fish oil (e.g., oleic, palmitic and/or linoleic acid).

The fortified bran food product of this invention is preferably prepared in multiple steps. The first step involves mixing the nutrients (i.e., the vitamins D, folic acid, selenium, calcium, magnesium, omega 3 fatty acids, and optionally zinc in the amounts recited above with the cereal bran, using appropriate mixing equipment. It is preferred that the fat based ingredients be in the form of a sprayed-dried, stabilized power; however, the Omega 3 fatty acids and Vitamin D may be in oil form. The resulting mixture should be substantially homogeneous and of substantially even particle size. An approved food-grade antioxidant may be added at this point to prevent degradation of the materials before stabilization. A flow aid may also be added to make the materials easier to mix. The mixture may be presented as a dry blend at this point or involve a second step involving coating the materials with a least one food-grade coating such as cellulose, gums, sugars, waxes or starch to seal the ingredients from oxygen and to stabilize them. It is preferred that the coating be applied in a microencapsulation process. Microencapsulation is a process by which small particles or droplets are surrounded by a coating to produce capsules in the micrometer to millimeter range, known as microcapsules. The material inside the capsule is referred to as the core, internal phase or fill, whereas the wall is sometimes called a shell, coating or membrane. Any conventional microencapsulation process may be used including spray drying, spray chilling, rotary disk atomization, fluid bed coating, stationary nozzle coextrusion, centrifugal head coextrusion and submerged nozzle coextrusion. It is preferred to use rotary disk atomization or fluid bed coating, more preferably fluid bed. The third step involves drying the mixture to a final moisture of from about 3% to about 5% by weight and homogenizing the particles.

An analytical assay should be taken to assure the minimum concentration of the required ingredients. The analysis may be performed by standard AOAC (Association of Official Agricultural Chemists) methods for grain or by specialized and validated solid phase extraction (SPE) and high pressure liquid chromatography HPLC) methods. In the case of specialized testing methods, extraction of the nutrients without destroying them is a critical step and requires methods not currently published by AOAC. An analysis of the crude and soluble fiber may, also be helpful for future studies on the fortified bran food product.

The food product of this invention may further contain one or more of flavors, coloring agents, spices and the like. Flavorings can be in the form of flavored extracts, volatile oils, chocolate flavorings, peanut butter flavoring, cookie crumbs, crisp rice, vanilla or any commercially available flavoring. Examples of suitable flavoring include but are not limited to pure anise extract, imitation banana extract, imitation cherry extract, chocolate extract, pure lemon extract, pure orange extract, pure peppermint extract, imitation pineapple extract, Imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil. Flavoring may optionally be encapsulated.

One or more sweeteners may be added in addition to the flavorings above. Non-limiting examples include natural and artificial sweeteners such as dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin and L-aspartyl L-phenylanine methyl ester.

One or more emulsifiers, surfactants, and flow aids may be added for stability of the final product. Examples of suitable emulsifiers, surfactants and flow aids include, but are not limited to, lecithin (e.g., from egg or soy), talc, magnesium stearate, calcium stearate, stearic acid, polyethylene glycol, sodium benzoate, sodium lauryl sulfate, magnesium lauryl sulfate, mono- and di-glycerides and/or silicon dioxide.

One or more preservatives and antioxidants may also be added to the food product to extend product shelf life. Non-limiting examples of suitable preservatives and antioxidants include potassium sorbate, sodium sorbate, potassium benzoate, sodium benzoate, ascorbic acid, citric acid, ascorbyl palmitate and/or calcium disodium EDTA.

The fortified bran food product of this invention is preferably in the form of a stabilized powder. As stated previously herein, the food product of this invention may be used as a dietary supplement or as an added ingredient to fortify food systems. Thus, another aspect of the present invention is directed to a food article comprising the fortified bran product of this invention. Non-limiting examples of food articles in which the food product of this invention may be used include beverages, snack bars, baked goods, cereal and puddings.

A further aspect of this invention is directed to a method for treating and/or preventing disorders of the digestive tract using the food product of this invention. The method involves orally administering a therapeutically effective amount of the food product to an animal, preferably a human, for a therapeutically effective period of time.

As used herein with respect to the amount of the food product administered to the animal, the term "therapeutically effective" means that amount of the product which will prevent and/or treat digestive disease in the animal. With respect to the period of time in which the animal is administered the product, the term "therapeutically effective" means that period of time which is sufficient to prevent and/or treat digestive disease in the animal.

The food product is preferably orally administered on a daily basis to the animal. In such instance, the food product is preferably administered in an amount of at least about 30 grams per day for a period of at least about 2 weeks. If the product is not administered on a daily basis, the amount and period of time will increase accordingly.

What is claimed is:

1. A fortified cereal bran food product for treating and/or reducing the risk of disorders of the digestive tract, comprising in admixture:
    a) cereal bran as a carrier;
    b) about 10 to 800 International Units of vitamin D per 30 grams of bran;
    c) about 20 to 200 mcg of selenium per 30 grams of bran;
    d) about 50 to 2000 mg of calcium per 30 grams of bran;
    e) about 10 to 500 mg of magnesium per 30 grams of bran;
    f) about 0.1 to 2 mg of folic acid per 30 grams of bran; and
    g) about 150 to 3000 mg of omega 3 fatty acids containing at least one of eicosapentaenoic acid and docosahexaenoic acid per 30 grams of bran;
    wherein said cereal bran can be comprised of one of a single cereal or a mixture of cereals.

2. A product of claim 1 wherein the bran is a bran of a cereal selected from the group consisting of wheat, rice, barley, sorghum, millet, rye, oats, and soy.

3. A product of claim 2 wherein the bran is not defatted.

4. A product of claim 2 wherein the bran is rice bran.

5. A product of claim 4 wherein the rice bran is not defatted.

6. A product according to claim 1, containing from about 25 to about 400 International Units of vitamin D, per 30 grams of the rice bran.

7. A product according to claim 1, containing from about 0.2 to about 2 mg of folic acid per 30 grams of the rice bran.

8. A product according to claim 1, containing from about 300 to about 1800 mg of calcium per 30 grams of the rice bran.

9. A product according to claim 1, containing from about 40 to about 350 mg of magnesium per 30 grams of the rice bran.

10. A product according to claim 1, containing from about 300 to about 1000 milligrams of omega-3-fatty acids per 30 grams of the rice bran.

11. A product according to claim 1 containing at least about 30 grams of the cereal bran.

12. A food article comprising the fortified bran food product of claim 1.

13. A method for treating and/or reducing the risk of disorders of the digestive tract in an animal, comprising
    (A) providing a fortified cereal bran food product comprising in admixture:
        a) cereal bran as a carrier;
        b) about 10 to 800 International Units of vitamin D per 30 grams of bran;
        c) about 20 to 200 mcg of selenium per 30 grams of bran;
        d) about 50 to 2000 mg of calcium per 30 grams of bran;
        e) about 10 to 500 mg of magnesium per 30 grams of bran;
        f) about 0.1 to 2 mg of folic acid per 30 grams of bran; and
        g) about 150 to 3000 mg of omega 3 fatty acids containing at least one of eicosapentaenoic acid and docosahexaenoic acid per 30 grams of bran;
    wherein said cereal bran can be comprised of one of a single cereal or a mixture of cereals;
    (B) orally administering to the mammal for a therapeutically effective period of time a therapeutically effective amount of the fortified bran food product.

14. The method of claim 13 wherein the bran is a bran of a cereal selected from the group consisting of wheat, rice, barley, sorghum, millet, rye, oats, and soy.

15. The method of claim 14 wherein the bran is not defatted.

16. The method of claim 14 wherein the bran is rice bran.

17. The method of claim 16 wherein the rice bran is not defatted.

18. The method of claim 13, containing from about 25 to about 400 International Units of vitamin D, per 30 grams of the rice bran.

19. The method of claim 13, containing from about 0.2 to about mg of folic acid per 30 grams of the rice bran.

20. The method of claim 13, containing from about 300 to about 1800 mg of calcium per 30 grams of the rice bran.

21. The method of claim 13, containing from about 40 to about 350 mg of magnesium per 30 grams of the rice bran.

22. The method of claim 13, containing from about 300 to about 1000 milligrams of omega-3-fatty acids per 30 grams of the rice bran.

23. The method of claim 13, containing at least about 30 grams of the cereal bran.

24. The method of claim 13, wherein the product is orally administered on a daily basis and the therapeutically effective period of time is at least about 2 weeks.

25. The method of claim 13, wherein the animal is a human.

* * * * *

UNITED STATES PATENT AND TRADEMARK OFFICE
CERTIFICATE OF CORRECTION

| | |
|---|---|
| PATENT NO. | : 7,700,142 B2 |
| APPLICATION NO. | : 11/130008 |
| DATED | : April 20, 2010 |
| INVENTOR(S) | : Diane W. Hoffpauer |

Page 1 of 1

It is certified that error appears in the above-identified patent and that said Letters Patent is hereby corrected as shown below:

Claim 19, column 7, line 10, please change "0.2 to about mg" to --0.2 to about 2.0 mg--.

Signed and Sealed this
Eighteenth Day of January, 2011

David J. Kappos
*Director of the United States Patent and Trademark Office*